US011690763B2

(12) United States Patent
Wu (10) Patent No.: US 11,690,763 B2
(45) Date of Patent: Jul. 4, 2023

(54) COMBINATION OF A GOGGLE AND A FACE MASK

(71) Applicant: TECMEN ELECTRONICS CO., LTD, Jiangsu (CN)

(72) Inventor: Ziqian Wu, Nanjing (CN)

(73) Assignee: TECMEN ELECTRONICS CO., LTD, Nanjing (CN)

( * ) Notice: Subject to any disclaimer, the term of this patent is extended or adjusted under 35 U.S.C. 154(b) by 79 days.

(21) Appl. No.: 16/615,789

(22) PCT Filed: Sep. 30, 2019

(86) PCT No.: PCT/CN2019/109313
§ 371 (c)(1),
(2) Date: Nov. 21, 2019

(87) PCT Pub. No.: WO2020/083010
PCT Pub. Date: Apr. 30, 2020

(65) Prior Publication Data
US 2020/0368068 A1 Nov. 26, 2020

(30) Foreign Application Priority Data

Oct. 23, 2018 (CN) .......................... 201811239716.1
Oct. 23, 2018 (CN) .......................... 201821720908.X (51) Int. Cl.
*A61F 9/06* (2006.01)
*A41D 13/11* (2006.01)

(52) U.S. Cl.
CPC .......... *A61F 9/067* (2013.01); *A41D 13/1184* (2013.01)

(58) Field of Classification Search
CPC .. A61F 9/067; A61F 9/029; A61F 9/06; A61F 9/04; A61F 9/022; A41D 13/1184; A41D 13/11; A62B 18/02

(Continued)

(56) References Cited

U.S. PATENT DOCUMENTS 3,298,031 A * 1/1967 Harold ............... A41D 13/1184
2/9
4,250,577 A * 2/1981 Smith .................. A62B 18/084
2/427

(Continued)

FOREIGN PATENT DOCUMENTS

AU 2012238227 B9 * 4/2014 ............. A61F 9/029
CN 1192162 A 9/1998

(Continued)

OTHER PUBLICATIONS

International Search Report and Written Opinion regarding Application No. PCT/CN2019/109313, dated Jan. 8, 2020, 10 pages.

(Continued)

*Primary Examiner* — Khoa D Huynh
*Assistant Examiner* — Aiying Zhao (57) ABSTRACT

The present application discloses an apparatus, comprising: a goggle, including a goggle frame and a protective lens installed in the goggle frame; a face mask releasably connected to the goggle; a detachable pivot-connection structure provided between two lateral sides of the goggle frame and the face mask, the detachable pivot-connection structure comprising a pivoting axis substantially parallel to a lateral direction of the goggle frame; and a detachable locking structure provided between the goggle frame and the face mask, the detachable pivot-connection structure configured to cooperate with the detachable pivot-connection structure to selectively lock the goggle frame and the face mask together.

20 Claims, 6 Drawing Sheets (58) Field of Classification Search
USPC .................................. 2/426, 427, 428, 429
See application file for complete search history.

(56) References Cited

U.S. PATENT DOCUMENTS

| | | | | |
|---|---|---|---|---|
| 4,884,302 | A * | 12/1989 | Foehl | A42B 3/222 |
| | | | | 2/424 |
| 5,692,522 | A | 12/1997 | Landis | |
| 6,065,833 | A * | 5/2000 | Tiano | A61F 9/029 |
| | | | | 2/435 |
| 6,401,716 | B1 | 6/2002 | Sword et al. | |
| 2006/0085883 | A1* | 4/2006 | Tan | A41D 13/1184 |
| | | | | 2/9 |
| 2007/0235031 | A1 | 10/2007 | Betz | |
| 2012/0060266 | A1 | 3/2012 | Stevens | |
| 2013/0014316 | A1 | 1/2013 | Castro et al. | |
| 2014/0007312 | A1* | 1/2014 | Wright | A61F 9/06 |
| | | | | 2/8.2 |
| 2017/0219843 | A1 | 8/2017 | Albouy | |

FOREIGN PATENT DOCUMENTS

| | | | | |
|---|---|---|---|---|
| CN | 205358329 | U | 7/2016 | |
| CN | 106796357 | A | 5/2017 | |
| CN | 107348574 | A * | 11/2017 | ......... A41D 13/1184 |
| CN | 107348574 | A | 11/2017 | |
| CN | 108024871 | A | 5/2018 | |
| CN | 109730830 | A | 5/2019 | |
| EP | 625344 | A2 * | 11/1994 | ............... A61F 9/02 |
| JP | H6-77716 | U | 11/1994 | |
| JP | 2009-532116 | A | 9/2009 | |

OTHER PUBLICATIONS

IP Australia, Examination Report No. 1 regarding Application No. 2019363904, dated Nov. 25, 2020, 5 pages.

IP Australia, Examination Report No. 2 dated Jun. 3, 2021, regarding Application No. 2019363904, 3 pages.

Japanese Patent Office Notice of Reasons for Refusal dated Oct. 14, 2021 regarding Application No. 2020-552369, 8 pages.

IP Australia, Examination Report No. 3 dated Oct. 27, 2021 regarding Application No. 2019363904, 4 pages.

Extended European Search Report dated Nov. 18, 2021 regarding Application No. 19876533.1, 7 pages.

Canadian Intellectual Property Office, Office Action dated Feb. 13, 2023 regarding Application No. 3,092,773, 5 pages.

\* cited by examiner

COMBINATION OF A GOGGLE AND A FACE MASK

CROSS-REFERENCE TO RELATED APPLICATIONS

This application is a 371 National Stage of International Application No. PCT/CN2019/109313 filed Sep. 30, 2019, which claims priority to Chinese Patent Application No. 201821720908.X, filed Oct. 23, 2018, and Chinese Patent Application No. 201811239716.1, filed Oct. 23, 2018, the disclosures of which are herein incorporated by reference in their entirety.

BACKGROUND

1. Field

The present application generally relates to an apparatus including a goggle and a face mask, especially for welding.

2. Description of Related Art

Goggles are widely used in various application fields to protect eyes. For instance, in the site of welding, a goggle provided with an auto-darkening filter can be used to protect an operator's eyes from any harmful rays and splashes during a welding operation. For instance again, when hazardous gases exist at the working site, a transparent goggle can be used to protect the operator's eyes from any damage.

Sometimes, besides the eyes, it is necessary to protect the face of the operator. However, it may be very troublesome to equip the operator with a protective helmet in some special working sites.

SUMMARY

The present application is aimed at proposing an apparatus including a goggle and a face mask such that the goggle can be worn and used separately and, if desired, the face mask can be assembled with the goggle reliably and conveniently, so as to provide protection for a user's face.

According to one aspect of the present application, an apparatus including a goggle and a face mask is provided, comprising: a goggle, having a goggle frame and a protective lens installed in the goggle frame; a face mask releasably connected to the goggle, wherein a detachable pivot-connection structure is provided between two lateral sides of the goggle frame and the face mask and has a pivoting axis substantially parallel to a lateral direction of the goggle frame, and wherein a detachable locking structure is provided between the goggle frame and the face mask to cooperate with the detachable pivot-connection structure to selectively lock the goggle frame and the face mask together.

Optionally, the detachable pivot-connection structure comprises a receptacle formed on either lateral side of the goggle frame and a pivoting part formed on either lateral side of the face mask, and the pivoting part is able to be releasably received by the receptacle so as to be pivotable relative to the later.

Optionally, the detachable locking structure comprises a fastening bolt releasably connected to the face mask and a threaded hole formed in the goggle, and the fastening bolt is able to be screwed into the threaded hole.

Optionally, the receptacle is substantially C-shaped in its cross-section, and the pivoting part is generally in the form of a pin such that the pin is able to be inserted into a notch of the C-shape by elastic deformation.

Optionally, the receptacle is designed to be anti-disengaged such that it cannot be released from the face mask if it is not screwed in the threaded hole.

Optionally, the detachable locking structure comprises a releasable snap-fit component pivotally connected to the face mask and a projection formed in the goggle, and the snap-fit is able to be snapped with the projection via pivoting such that the goggle and the mask are locked together.

Optionally, the projective lens comprises an auto-darkening filter.

Optionally, the detachable pivot-connection structure comprises a receptacle formed on either lateral side of the face mask and a pivoting part formed on either lateral side of the goggle, and the pivoting part is able to be releasably received by the receptacle so as to be pivotable relative to the later.

Optionally, the opening of the C-shape is formed upwards or obliquely upwards.

Optionally, a first contact wall is formed in a lower side of the goggle frame, and the threaded hole is formed in the first contact wall; wherein the face mask has a second contact wall in which a through-hole is formed, and the fastening bolt is insertable into the through-hole such that as the goggle frame is being pivoted relative to the face mask, the first contact wall is able to approach the second contact wall.

The apparatus of the present application can be conveniently and flexibly used by the user in the site of welding. For example, if it is not necessary to wear the face mask, only the goggle can be worn on the head of the user. If it is necessary to protect the entire face of the user, it is rapid and reliable to connect the face mask to the goggle.

BRIEF DESCRIPTION OF THE DRAWINGS

The fore and other aspects of the present application will be well understood by the following description in combination with the attached drawings. It should be understood that although the drawings may be given in differential ratios, understanding to the present application is not affected. In the drawings.

DETAILED DESCRIPTION

In the drawings of the present application, features having similar or identical configurations or functions are represented by the same reference numerals respectively.

Figure 1:
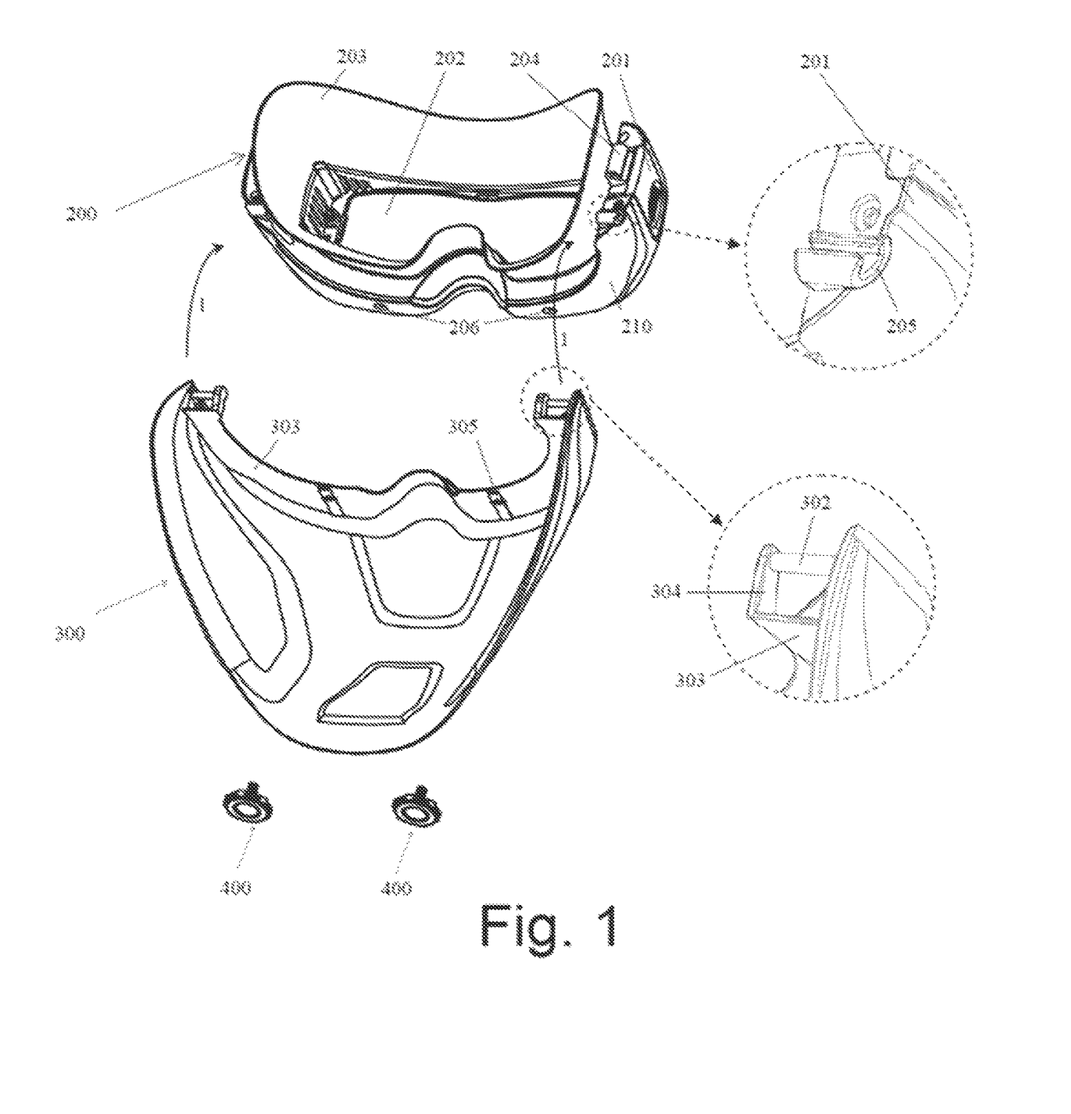
FIG. 1 is an exploded view schematically illustrating an embodiment of an apparatus including a goggle and a face mask according to the present application.

FIG. 1 is an exploded view schematically illustrating an apparatus 100 of including a combination of a goggle and a face mask according to an embodiment of the present application. The apparatus 100 comprises the goggle 200 and the face mask 300. The goggle 200 comprises a goggle frame 201 generally made of a plastic material. The goggle frame 201 includes a top surface, a bottom surface that is opposite the top surface of the goggle frame, a front surface, and a back surface that is opposite the front surface of the goggle frame. A goggle lens 202 is installed in the goggle frame 201 positioned near to the front surface. In the present application, the goggle lens 202 can be an auto-darkening filter or a transparent protective sheet. A protective cushion 203 can be applied over the goggle frame 201, by which protective cushion the surrounding tissue of eyes of a user, who wears the goggle 200, can be protected. The protective cushion 203 can be made of any suitable flexible material.

Respectively formed on two laterally opposing sides of the goggle frame 201 are two hook parts 204, for connecting with both ends of an elastic belt by which the goggle 200 can be readily secured onto the user's head. Two receptacles 205 are also formed on the two laterally opposing sides of the goggle frame 201 respectively such that the receptacles are disposed symmetrically relative to a median plane of the goggle 200. It should be noted that in the context of the present application, the term "lateral(ly)" when used for the goggle 200 (or the face mask 300) or their component usually refers to a left-right direction relative to the head of the user who wears the goggle (or the face mask). In FIG. 1, a dotted circle of the goggle frame 201 shows the right receptacle 205 in an enlarged manner respectively.

In the present application, the face mask 300 can be a half face mask including a top surface along a top edge of the face mask 300, a bottom surface that is opposite the top surface, an inner wall, and an external surface opposite the inner wall. That is, the mask has an area which conceals a face zone under the eyes of the user. In the context of the present application, the term "above" refers to a direction or orientation defined relative to the user's body (or head) height. For example, one feature is above another feature means that the one feature is at a level higher than the another feature along the user's body (or head) height. The term "below" refers to a direction or orientation defined relative to the user's body (or head) height. For example, one feature is below another feature means that the one feature is at a level lower than the another feature along the user's body (or head) height. A contact wall 210 is formed on a lower side of the goggle frame 201 of the goggle 200 such as the bottom surface of the goggle frame 201. The contact wall 210 is concaved at its middle part, so as to partially receive the user's nose bridge.

Two pivoting parts 302 are formed on laterally opposing sides of the face mask 300 respectively. The pivoting parts are symmetrical relative to a median plane of the face mask 300. In FIG. 1, a dotted circle of the face mask 300 shows the right pivoting part 302 in an enlarged manner. The pivoting part 302 is in the form of a pin extending inwards from an inner wall of the face mask 300. In the context of the present application, the term "inner/inwards" generally refers to a direction or orientation facing towards the user's body or head, and the term "outer/outwards" generally refers to a direction or orientation facing away from the user's body or head.

A contact wall 303 extends horizontally from an inner wall of the face mask 300 and is spaced from the pivoting parts 302. The two pivoting parts 302 are located adjacent to opposing ends of the contact wall 303 respectively. A support wall 304 extends from each end of the contact wall 303 and is substantially parallel to the inner wall of the face mask 300, so as to connect a respective pivoting part 302.

The contact wall 303 is shaped conforming to the contact wall 210 of the goggle 200, such that when the goggle 200 and the face mask 300 are assembled together the contact walls 210 and 303 can be at least partially in contact with each other. The receptacles 205 of the goggle 200 extend from the goggle frame 201 and are in the form of a notched tube. That is, the receptacle 205 has a C-shaped cross-section. Especially, the notch of the C-shape has a size slightly less that the diameter of the pivoting part 302. Therefore, the pivoting part 302 can be squeezed into the receptacle 205 in the form of the notched tube by expanding and deforming the notch of the C-shape, such that the pivoting part 302 can be pivotally received in the receptacle 205. If desired, by pulling the pivoting part 302 from the receptacle, they can be detached from each other. In this way, the two receptacles 205 of the goggle 200 and the pivoting parts 302 of the face mask 300 can be configured such that they can be pivotally engaged with each other, as mentioned above, and thus the receptacles 205 and the two respective pivoting parts 302 constitute a detachable pivot-connection structure. This detachable pivot-connection structure has a pivoting axis substantially parallel to a lateral direction of the goggle 200, especially its goggle frame 201. In an alternative embodiment, the pivoting parts and the receptacles of the detachable pivot-connection structure can be swapped with each other. For example, alternatively, the pivoting parts can be provided in the goggle 200 and the receptacles can be provided in the face mask 300.

The notch of the C-shape of each receptacle 205 of the goggle 200 is oriented upwards or obliquely upwards, so that when the goggle lens 202 of the goggle 200 is substantially perpendicular to the ground and the pivoting parts 302 have been inserted into the C-shapes' notches, the face mask 300 cannot fall off the goggle 200 because of gravity.

Two threaded holes 206 are formed in the contact wall 210 of the goggle 200, such that they are located symmetrically at both sides of the middle concave of the contact wall 210, respectively. Correspondingly, two through-holes 305 are formed in the contact wall 303 of the face mask 300, such that when the contact walls 210 and 303 are aligned with each other, the threaded holes 206 and the through-holes 305 can be aligned with each other respectively. A fastening bolt 400 can be inserted through each through-hole 305.

Figure 4:
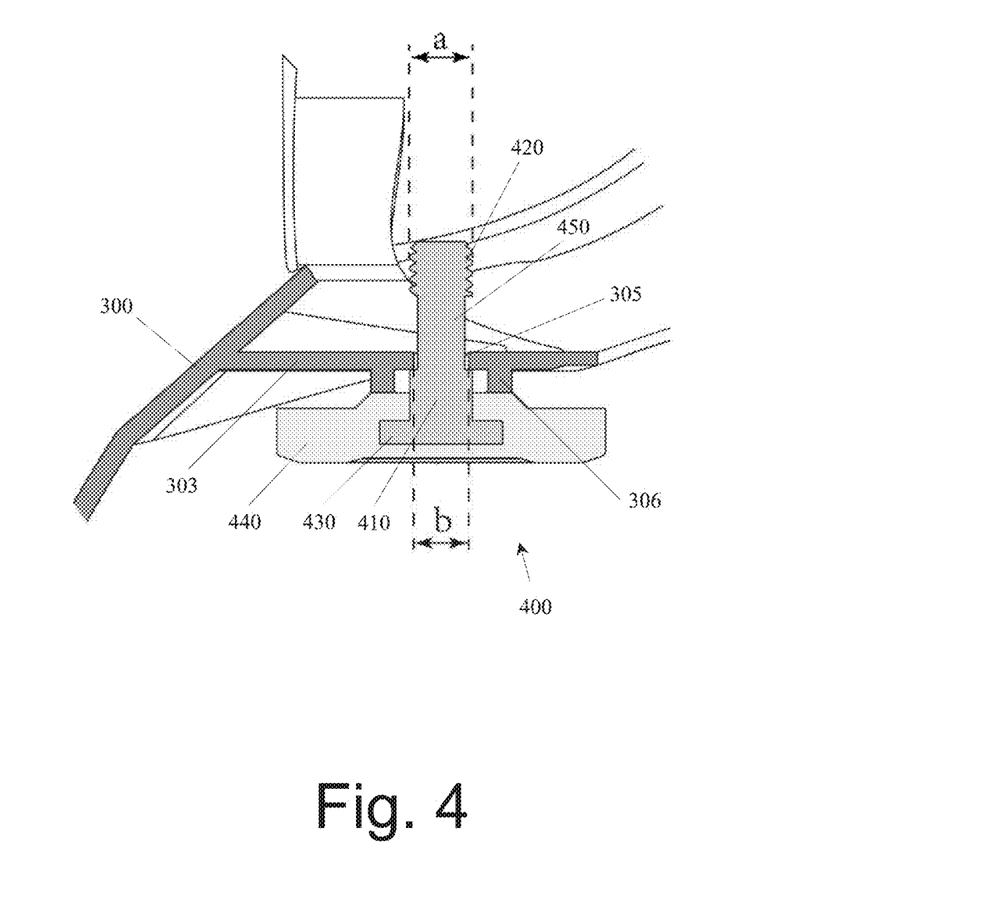
FIG. 4 is a cross-sectional view schematically illustrating a part of the face mask of the apparatus of FIG. 1.

Further as shown by FIG. 4, the fastening bolt 400 comprises a stem 410. For instance, the stem 410 can be made of a metallic material, so as to provide an improved locking strength. The stem 410 is formed with a threaded part 420 at one end, so as to be screwed into the respective threaded hole 206. The stem is formed with a head 430 at the opposite other end, by which head the stem 410 can be rotated. The threaded part 420 has an external diameter a slightly greater than an internal diameter b of the through-hole 305. Furthermore, a diameter-reduction section 450 is formed in the stem 410 between the threaded part 420 and the head 430. The diameter-reduction section 450 has a diameter less than the internal diameter b of the through-hole 305, such that when the threaded part 420 of the stem 410 is forced through the through-hole 305, the diameter-reduction section 450 is located in the through-hole 305 and thus the stem 410 is freely rotatable therein. Therefore, the fastening bolt 400 can provide not only a fastening function but also an anti-disengaging design. Optionally, an operating cap 440 can be over-molded by a plastic material onto the head 430, which facilitates the user to manually rotate the fastening bolt 400. If desired, by forcefully pulling the operating cap 440 of the fastening bolt 400, the threaded part 420 can be forced through the through-hole 305 again such that the fastening bolt 400 can be disengaged from the face mask 300. Then, by pulling the pivoting part 302 out of the receptacle 205, the apparatus 100 is disassembled.

As shown by FIG. 4, at a side of the contact wall 303 facing towards the head 430, a ring of flange 306 is formed around the through-hole 305, against which ring of flange the operating cap 440 made of the plastic material is able to abut during fastening.

Figure 2A:
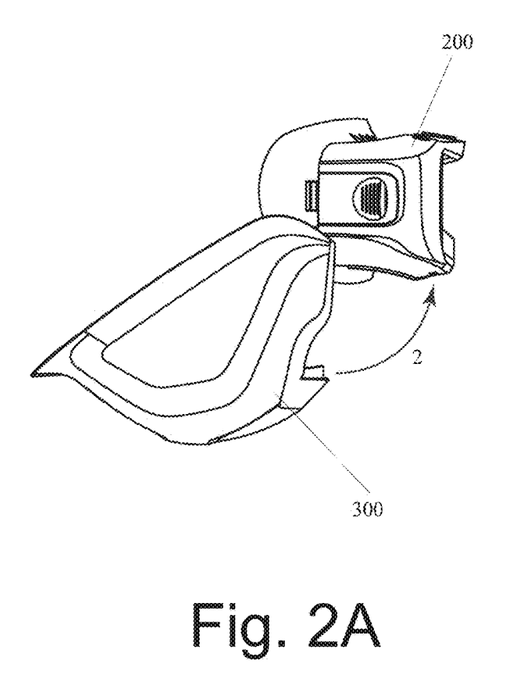
FIGS. 2A and 2B schematically illustrate how the goggle and the face mask of FIG. 1 are assembled together.
Figure 2B:
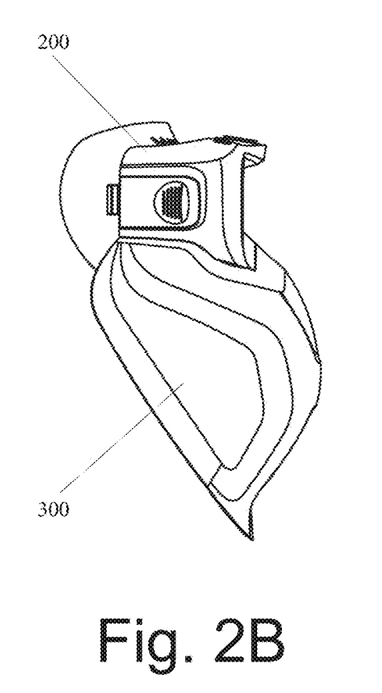
Figure 3:
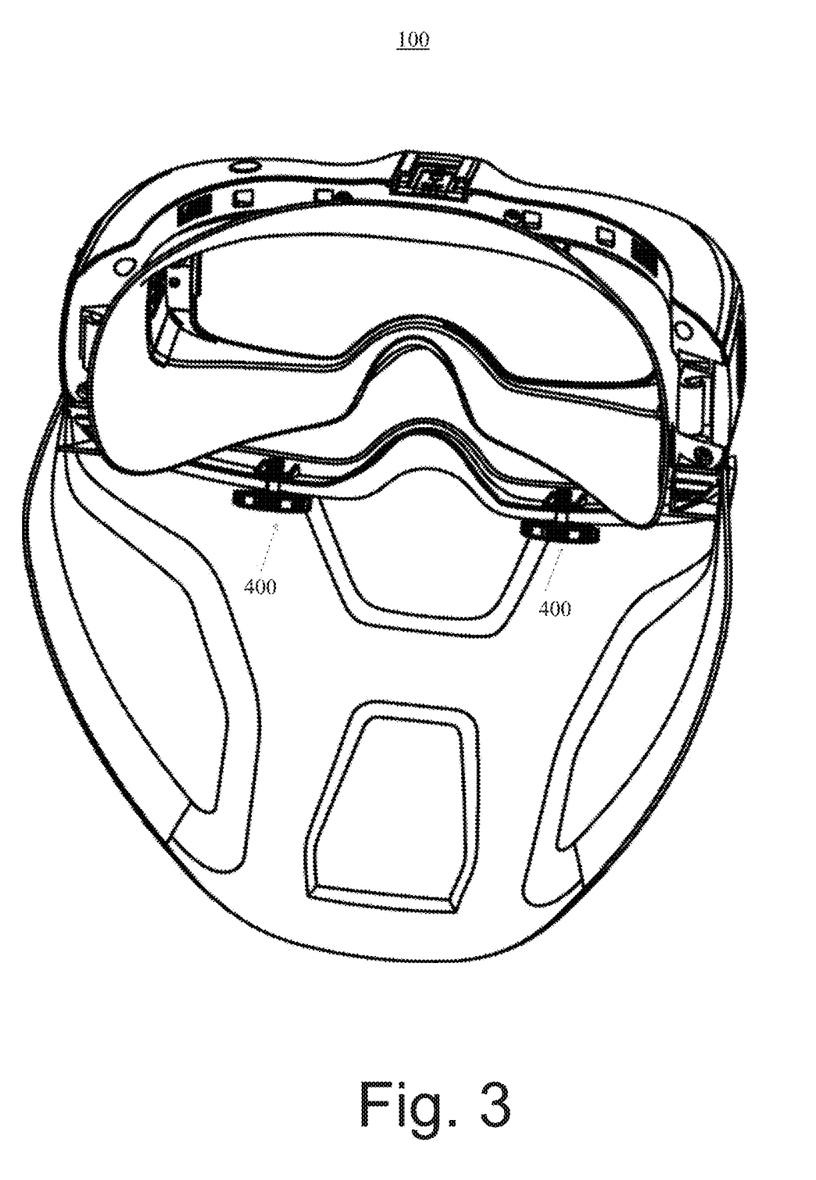
FIG. 3 is an overall view schematically illustrating the apparatus including the goggle and the face mask of FIG. 1.

Now, how to assemble the apparatus 100 of the goggle and the face mask according to the present application will be explained with respect to FIGS. 1 to 3 below. First, the goggle 200 is pivotally connected to the face mask 300, for example by inserting the pivoting parts 302 of the face mask 300 into the C-shaped receptacles 205 of the goggle 200, as illustrated by arrows 1. Optionally, it is feasible to releasably install the fastening bolt 400 into the face mask 300 beforehand or ex post, for example by inserting it into the through-hole 305. As the C shapes' notches of the C-shaped receptacles 205 of the goggle 200 are oriented upwards or obliquely upwards, the pivoting parts 302 are inserted into the C-shaped receptacles 205 of the goggle 200 generally in such a way that the contact wall 303 of the face mask 300 departs from the contact wall 210 of the goggle 200. Then, as shown, the face mask 300 is pivoted towards the goggle 200 about the pivoting axis of the pivot-connection structure formed by the pivoting parts 302 and the C-shaped receptacles 205 as shown by the arrow 2 of FIG. 2A, such that the contact wall 303 of the face mask 300 approaches the contact wall 210 of the goggle 200 and then they are in contact with each other, as shown by FIG. 2B. Then, by rotating the operating cap 440 of the fastening bolt 400, the threaded part 420 of the fastening bolt 400 is screwed into the threaded hole 206 of the goggle 200 such that the operating cap 440 abuts against the flange 306 adjacent to the through-hole 305 of the face mask 300. Finally, by the threaded fastening force, the goggle 200 and the face mask 300 can be locked to each other. In this way, the apparatus 100 including the goggle and the face mask can be assembled in place. If desired, by unscrewing the fastening bolt 400 and then removing the pivoting parts 302 from the C-shaped receptacles 205, the apparatus 100 including the goggle and the face mask can be disassembled.

It should be understood by the ordinary person in the art that although in the already-mentioned embodiments of the present application two fastening bolts 400 and two threaded holes 206 of the goggle 200 constitute a detachable locking structure, the number of the fastening bolts 400 and/or the threaded holes 206 is not limited to two. For instance, alternatively, only one fastening bolt 400 can be provided to engage with one threaded hole 206 of the goggle 200 so as to constitute the detachable locking structure. In an alternative embodiment, more than two fastening bolts 400 can be provided or more than two threaded holes 206 can be provided in the goggle 200.

Figure 5:
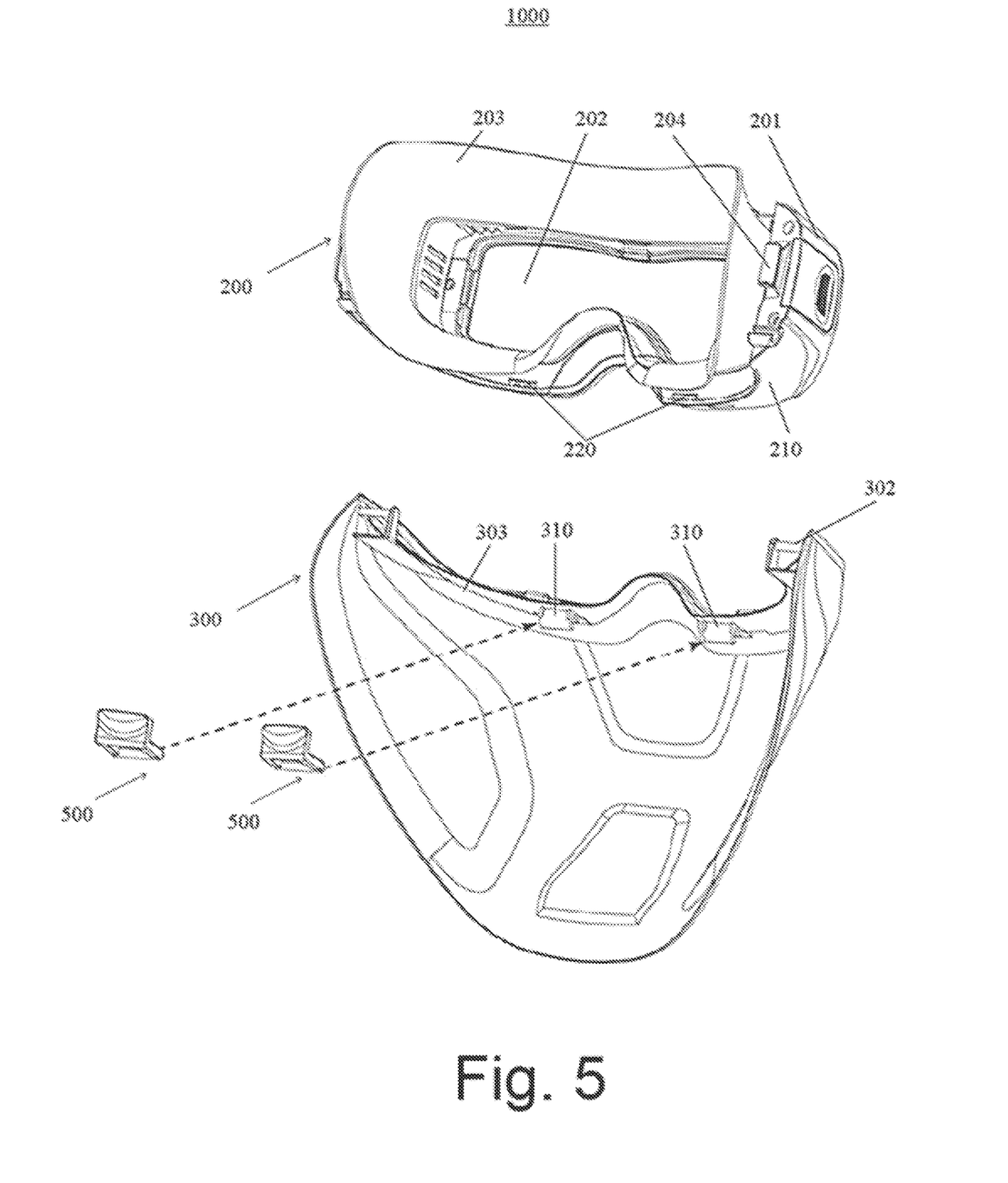
FIG. 5 is an exploded view schematically illustrating another embodiment of apparatus including a goggle and a face mask according to the present application.

FIG. 5 is an exploded view schematically illustrating an apparatus 1000 including a goggle and a face mask according to another embodiment of the present application. Regarding similar contents between the apparatus 1000 and the already-explained apparatus 100, please refer to the above description. Now, only the difference between them will be substantially explained below.

In the apparatus 1000 including the goggle and the face mask, two snap-fit components 500 are used to replace the fastening bolts 400 of the apparatus 100. Furthermore, two hook parts 310 are formed on a lower side of a contact wall 303 of the face mask 300 of the apparatus 1000 respectively.

In the meanwhile, two projections 220 are formed adjacent to an edge of a contact wall 210 of the goggle 200 of the apparatus 1000. The two hook parts 310 and the two projections 220 are positioned such that when the contact walls 303 and 210 are in contact with each other, the hook parts and the projections are aligned with each other respectively. Each snap-fit component 500 is generally L-shaped in its cross-section, wherein an arm of the L-shape is formed with an opening such that it can be hooked onto the hook part 310 and thus the snap-fit component 500 can be pivoted about the hook part 310. When the face mask 300 and the goggle 200 has been pivotally connected to each other as shown by FIG. 2B, the snap-fit components 500 can be hooked onto the hook parts 310 via their openings and be pivoted about the later (as illustrated by an arrow 3 of FIG. 6) until the other arm of the L-shape of the snap-fit components 500 engages with the corresponding projection 220. In this way, by a contact force exerted by the snap-fit components 500 on both the projections 220 and the hook parts 310, the goggle 200 and the face mask 300 can be locked to each other. Therefore, the apparatus 1000 including the goggle and the face mask can be assembled.

Figure 6:
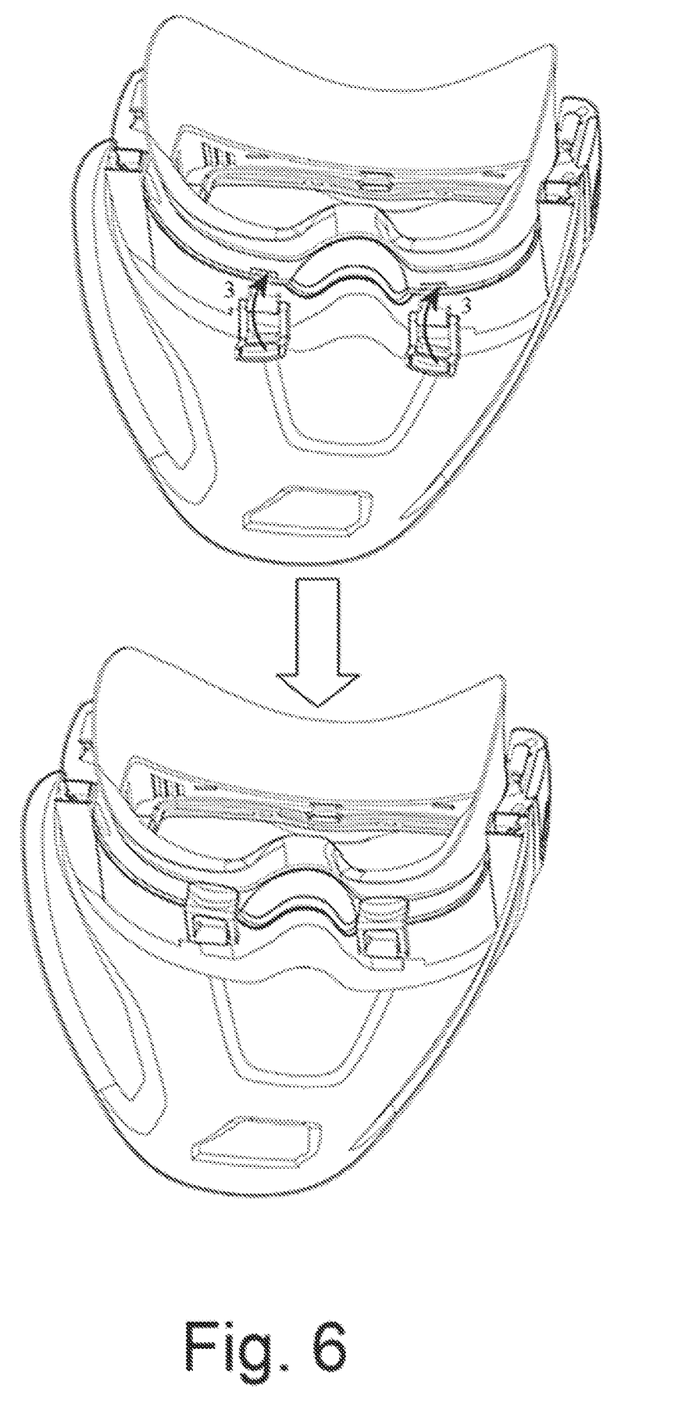
FIG. 6 schematically illustrates a process for assembling the apparatus including the goggle and the face mask of FIG. 5.

If desired, by pulling the snap-fit components 500 such that they disengage from the projections 220 and then the snap-fit components 500 can be removed from the goggle 200 and the face mask 300, the goggle 200 can be unlocked from the face mask 300. Then, by pulling the pivoting parts 302 out of the receptacles 205, the apparatus 1000 can be disassembled.

In the context of the present application, various embodiments can be arbitrarily combined with each other. Although some specific embodiments are described here, they are given out for illustrative purposes only and cannot be deemed to constrain the scope of the present application. Without departing from the spirit and scope of the present application, various replacements, alternations and modifications can be thought out.

The invention claimed is:

1. An apparatus comprising:
   a goggle including:
      a goggle frame including a top surface and a first contact wall at a bottom surface of the goggle frame that is opposite the top surface of the goggle frame, and a protective lens installed in the goggle frame;
   a face mask releasably connected to the goggle, the face mask including a second contact wall, a top surface, and a bottom surface that is opposite the top surface of the face mask, the second contact wall extending horizontally from an inner wall of the face mask a distance below the top surface of the face mask when the face mask is worn;
   a detachable connection comprising a pivoting axis parallel to a lateral direction of the goggle frame; and
   a locking connection provided between the bottom surface of the goggle frame and the second contact wall of the face mask, the locking connection configured to cooperate with the detachable connection to selectively lock the bottom surface of the goggle frame to the second contact wall of the face mask along the lateral direction by securing a portion of the first contact wall to a portion of the second contact wall.

2. The apparatus of claim 1, wherein:
   a shape of the second contact wall conforms to a shape of the first contact wall, the first and second contact walls are at least partially in contact with each other when the face mask is selectively locked to the goggle frame by the locking connection, the detachable connection comprises:
- a receptacle formed on a side of the goggle frame; and
- a pin extending along the pivoting axis formed on a side of the face mask and configured to be releasably received by the receptacle in a manner that is pivotable relative to the receptacle.

3. The apparatus of claim 2, wherein the locking connection comprises:
- a threaded hole formed in the goggle; and
- a fastening bolt releasably connected to the face mask and configured to be screwed into the threaded hole.

4. The apparatus of claim 3, wherein the protective lens comprises an auto-darkening filter.

5. The apparatus of claim 3, wherein:
- the threaded hole is formed in the first contact wall;
- the second contact wall includes a through-hole; and
- the fastening bolt is insertable into the through-hole and into the threaded hole, affixing the first contact wall to the second contact wall.

6. The apparatus of claim 3, wherein the goggle frame is secured to the face mask when the fastening bolt is releasably connected to the face mask and screwed into the threaded hole.

7. The apparatus of claim 6, wherein:
- the threaded hole is formed in the first contact wall;
- the second contact wall includes a through-hole; and
- the fastening bolt is insertable into the through-hole and into the threaded hole, affixing the first contact wall to the second contact wall.

8. The apparatus of claim 6, wherein the protective lens comprises an auto-darkening filter.

9. The apparatus of claim 2, wherein:
- a cross-section of the receptacle is substantially C-shaped; and
- the pin is configured to be inserted into a notch of the C-shaped receptacle by elastic deformation.

10. The apparatus of claim 9, wherein an opening of the C-shaped receptacle is formed upwards or obliquely upwards.

11. The apparatus of claim 2, wherein the locking connection comprises:
- a projection formed in the goggle; and
- a releasable snap-fit component pivotally connected to the face mask and configured to be connected with the projection via pivoting in a manner that the goggle and the face mask are locked together.

12. The apparatus of claim 11, wherein the protective lens comprises an auto-darkening filter.

13. The apparatus of claim 1, wherein the detachable connection comprises:
- a receptacle formed on a side of the face mask; and
- a pin extending along the pivoting axis formed on a side of the goggle and configured to be releasably received by the receptacle in a manner that is pivotable relative to the receptacle.

14. The apparatus of claim 1, wherein the locking connection comprises:
- a threaded hole formed in the goggle; and
- a fastening bolt releasably connected to the face mask and configured to be screwed into the threaded hole.

15. The apparatus of claim 14, wherein the fastening bolt comprises a stem configured to be screwed into the threaded hole.

16. The apparatus of claim 15, wherein the stem comprises:
- a threaded part configured to be screwed into the threaded hole; and
- a head disposed opposite of the threaded part, wherein the head is inserted into an operating cap.

17. The apparatus of claim 16, wherein the operating cap is configured to allow the fastening bolt to be rotated or removed from the threaded hole.

18. The apparatus of claim 1, wherein the locking connection comprises:
- a projection formed in the goggle; and
- a releasable snap-fit component pivotally connected to the face mask and configured to be connected with the projection via pivoting in a manner that the goggle and the face mask are locked together.

19. The apparatus of claim 18, wherein the protective lens comprises an auto-darkening filter.

20. The apparatus of claim 1, further comprising:
- a first support wall extending from a first end of the second contact wall and substantially parallel to the inner wall of the face mask, and
- a second support wall extending from a second end of the second contact wall and substantially parallel to the inner wall of the face mask, wherein:
- the protective lens comprises an auto-darkening filter, and
- the detachable connection including a first portion and a second portion, wherein the first portion detachably connects a left side of the goggle to a left side of the face mask and the second portion detachably connects a right side of the goggle to a right side of the face mask.

* * * * *